US009005599B2

(12) United States Patent
Ennis et al.

(10) Patent No.: US 9,005,599 B2
(45) Date of Patent: Apr. 14, 2015

(54) GENETICALLY MODIFIED HUMAN UMBILICAL CORD PERIVASCULAR CELLS FOR PROPHYLAXIS AGAINST OR TREATMENT OF BIOLOGICAL OR CHEMICAL AGENTS

(75) Inventors: Jane Elizabeth Ennis, Oakville (CA); Jeffrey Donald Turner, Chute-a-Blondeau (CA); John Edward Davies, Toronto (CA)

(73) Assignee: Tissue Regeneration Therapeutics Inc., Toronto (CA)

( * ) Notice: Subject to any disclaimer, the term of this patent is extended or adjusted under 35 U.S.C. 154(b) by 48 days.

(21) Appl. No.: 12/988,909

(22) PCT Filed: Apr. 20, 2009

(86) PCT No.: PCT/CA2009/000528
§ 371 (c)(1),
(2), (4) Date: Mar. 21, 2011

(87) PCT Pub. No.: WO2009/129616
PCT Pub. Date: Oct. 29, 2009

(65) Prior Publication Data
US 2011/0177023 A1  Jul. 21, 2011

Related U.S. Application Data

(60) Provisional application No. 61/046,630, filed on Apr. 21, 2008.

(51) Int. Cl.
| | |
|---|---|
| A61K 38/20 | (2006.01) |
| A61K 35/12 | (2006.01) |
| C12N 5/071 | (2010.01) |
| A61K 39/00 | (2006.01) |
| A61K 38/21 | (2006.01) |
| A61P 37/04 | (2006.01) |
| A61P 37/06 | (2006.01) |
| C07K 14/56 | (2006.01) |
| A61K 35/44 | (2006.01) |
| A61K 39/12 | (2006.01) |
| C07K 16/10 | (2006.01) |
| C12N 5/073 | (2010.01) |
| C12N 5/0775 | (2010.01) |

(52) U.S. Cl.
CPC ............... *C07K 14/56* (2013.01); *A61K 35/44* (2013.01); *A61K 39/12* (2013.01); *A61K 2035/124* (2013.01); *A61K 2039/505* (2013.01); *A61K 2039/5156* (2013.01); *C07K 16/1081* (2013.01); *C12N 2510/00* (2013.01); *C12N 2760/14134* (2013.01); *C12N 2770/36134* (2013.01); *C12N 5/0605* (2013.01); *C12N 5/0668* (2013.01)

(58) Field of Classification Search
CPC ........................................................ C07K 14/56
See application file for complete search history.

(56) References Cited

U.S. PATENT DOCUMENTS

| | | | |
|---|---|---|---|
| 5,158,867 | A | 10/1992 | McNally et al. |
| 5,919,702 | A | 7/1999 | Purchio et al. |
| 7,122,178 | B1 | 10/2006 | Simmons et al. |
| 7,547,546 | B2 | 6/2009 | Davies et al. |
| 2003/0161818 | A1 | 8/2003 | Weiss et al. |
| 2004/0136967 | A1 | 7/2004 | Weiss et al. |
| 2004/0137612 | A1 | 7/2004 | Baksh et al. |
| 2005/0019911 | A1 | 1/2005 | Gronthos et al. |
| 2004/1396967 | | 7/2005 | Weiss et al. |
| 2005/0148074 | A1 | 7/2005 | Davies et al. |
| 2005/0158289 | A1 | 7/2005 | Simmons et al. |
| 2005/0281790 | A1 | 12/2005 | Simmons et al. |
| 2006/0008452 | A1 | 1/2006 | Simmons et al. |
| 2006/0193840 | A1 | 8/2006 | Gronthos et al. |
| 2006/0199263 | A1 | 9/2006 | Auger et al. |
| 2006/0286077 | A1 | 12/2006 | Gronthos et al. |
| 2007/0134205 | A1 | 6/2007 | Rosenberg |
| 2008/0020459 | A1 | 1/2008 | Baksh et al. |
| 2008/0113434 | A1 | 5/2008 | Davies et al. |
| 2009/0047277 | A1 | 2/2009 | Reed et al. |
| 2009/0269318 | A1 | 10/2009 | Davies et al. |
| 2009/0275127 | A1 | 11/2009 | Ennis et al. |
| 2009/0285842 | A1 | 11/2009 | Davies et al. |

FOREIGN PATENT DOCUMENTS

| | | |
|---|---|---|
| WO | WO 01/11011 | 2/2001 |
| WO | WO 02/086104 | 10/2002 |
| WO | WO 2004/072273 | 8/2004 |
| WO | 2004/094599 | 11/2004 |
| WO | WO-2004/094599 A2 | 11/2004 |
| WO | WO 2005/001076 | 1/2005 |
| WO | WO 2005/027633 | 3/2005 |
| WO | WO 2005/038012 | 4/2005 |

(Continued)

OTHER PUBLICATIONS

Friedman et al. (Biology of Blood and Marrow Transplantation. 2000; 13(12): 1477-1486).*

(Continued)

*Primary Examiner* — Scott Long
(74) *Attorney, Agent, or Firm* — Clark & Elbing LLP; Paul T. Clark, Esq.; Todd Armstrong

(57) ABSTRACT

The invention provides methods of preventing or treating diseases or disorders caused by biological agents or chemical agents in a subject (e.g., a mammal, such as a human) by administering genetically modified human umbilical cord perivascular cells.

16 Claims, No Drawings

(56) References Cited

FOREIGN PATENT DOCUMENTS

| WO | WO-2006/002627 A2 | 1/2006 | | |
|----|----|----|----|----|
| WO | 2006/012404 | 2/2006 | | |
| WO | WO-2006/012404 A2 | 2/2006 | | |
| WO | WO 2006/019357 | 2/2006 | | |
| WO | WO 2005/085428 | 6/2007 | | |
| WO | WO 2007/071048 | 6/2007 | | |
| WO | WO 2007/099534 | 9/2007 | | |
| WO | WO2007/128115 | * 11/2007 | ............ | A61K 35/44 |
| WO | WO 2007/128115 | 11/2007 | | |

OTHER PUBLICATIONS

Wolbank et al. (Cell Tissue Banking. 2007; 8:163-177).*
Lu et al. (J Lab Clin Med. 2005; 146(5): 271-278).*
Silva et al (TRENDS in Molecular Medicine. Nov. 2002; 8(11): 505-508).*
Nilsson et al. (Journal of Infectious Diseases. 1999; 180: 1370-1373).*
Patocka et al (Defence Science Journal. 2006; 56(5): 775-784).*
Saxena et al. "Chapter 7. Novel Approaches to Medical Protection against Chemical Warfare Nerve Agents." Chemical Warfare Agents (CRC Press 2007) pp. 145-174).*
Blong et al., Biochem. J. 327:747-757, 1997.*
Kronman et al., J. Biol. Chem. 275:29488-29502, (2000).*
Huang et al., Proc. Nat'l. Acad. Sci. USA 104:13603-13608,2007.*
Li et al., Chemico-BiologicalInter. 187:101-105, 2010.*
Geyer et al., Proc. Nat'l. Acad. Sci. USA 107:20251-20256, 2010.*
Li et al. (Biochem J. 411: 425-432, 2008).*
Schneider et al. (Biotechnol. J. 9:501-510, 2014).*
Ilyushin et al. (Proc. Nat'l Acad. Sci. USA 110:1243-1248,2013.*
Chilukuri etal. (Chem. Biol. Interact. 157-158:115-121, 2005).*
Saxena (Chemical Warfare Agents, CRC Press 2007, pp. 145-174).*
Chilukuri et al. (Mol Pharmacal. 76(3): 612-617, 2009).*
Parikh et al. (J Pharmacal Exp Ther. 337(1): 92-101, 2011).*
Capasso et al. (Viruses 6: 832-855, 2014).*
Hendrickx et al. (Hum Gene Ther,. 25(4): 265-84, 2014).*
Nachon et al. (Chem Biol Interact. 206(3): 536-44, 2013).*
Brazzolotto et al., (FEBS J. 279(16): 2905-2916, 2012).*
Lockridge et al. (J Med Chern Biol Radial Oef. 3, 2005).*
Ilyushin et al. (Acta Naturae (16): 73-84, 2013).*
Aggarwal et al., "Human Mesenchymal Stem Cells Modulate Allogeneic Immune Cell Responses," *Blood* 105:1815-1822 (2005).
Aubin, "Bone Stem Cells," *J. Cell Biochem. Suppl.* 30-31:73-82 (1998).
Baksh et al., "Comparison of Proliferative and Multilineage Differentiation Potential of Human Mesenchymal Stem Cells Derived from Umbilical Cord and Bone Marrow," *Stem Cells* 25:1384-1392, (2007).
Beckstead et al., "Enzyme Histochemistry and Immunohistochemistry on Biopsy Specimens of Pathologic Human Bone Marrow," *Blood* 57:1088-1098 (1981).
Beckstead et al., "Enzyme Histochemistry and Immunohistochemistry on Bone Marrow Biopsies: Reactions Useful in the Differential Diagnosis of Leukemia and Lymphoma Applied to 2-Micron Plastic Sections," *Blood* 55:386-394 (1980).
Bianco et al., "Uno, Nessuno e Centomila: Searching for the Identity of Mesodermal Progenitors," *Experimental Cell Research* 251 :257-263 (1999).
Bieback et al., "Critical Parameters for the Isolation of Mesenchymal Stem Cells from Umbilical Cord Blood," *Stem Cells* 22;625-634 (2004).
Can et al., "Concise Review: Human Umbilical Cord Stroma with Regard to the Source of Fetus-Derived Stem Cells," *Stem Cells* 25:2886-2895 (2007).
Canfield et al., "Osteogenic Potential of Vascular Pericytes" *Bone Engineering*, JE Davies, Toronto, EM Squared 143-151 (2000).
Caplan, "Mesenchymal Stem Cells," *J. Orthop. Res.* 9:641-650 (1991).

Chacko and Reynolds, "Architecture of Distended and Nondistended Human Umbilical Cord Tissues, with Special Reference to the Arteries and Veins," Carnegie Institute of Washington, *Contributions to Embryology* 35:135-150 (1954).
Conget and Minguell, "Phenotypical and Functional Properties of Human Bone Marrow Mesenchymal Progenitor Cells," *J. Cell Physiol.* 181:67-73 (1999).
Corcione et al., "Human Mesenchymal Stem Cells Modulate B-Cell Functions," *Blood* 107:367-372 (2006).
Di Nicola et al., "Human Bone Marrow Stromal Cells Suppress T-Lymphocyte Proliferation Induced by Cellular or Nonspecific Mitogenic Stimuli," *Blood* 99:3838-3843 (2002).
Djouad et al., "Immunosuppressive Effect of Mesenchymal Stem Cells Favors Tumor Growth in Allogenic Animals," *Blood* 102:3837-3844 (2003).
Ennis et al., "Isolation, Characterization, and Differentiation of Human Umbilical Cord Perivascular Cells (HUCPVCs)," *Meth. in Cell Biol.* 86:121-136, (2008).
Etherington, "Proteinases in Connective Tissue Breakdown." *Ciba Found. Symp.* 75:87-103 (1979). [Abstract Only].
Friedenstein et al., "Fibroblast Precursors in Normal and Irradiated Mouse Hematopoietic Organs," *Exp. Hematol.* 4:267-274 (1976).
Friedman et al., "Umbilical Cord Mesenchymal Stem Cells: Adjuvants for Human Cell Transplantation," *Biol. Blood Marrow Transplant.* 13:1477-1486 (2007).
Gronthos et al., "Postnatal Human Dental Pulp Stem Cells (DPSCs) in vitro and in vivo." *Proc. Natl. Acad. Sci. USA* 97(25):13625-13630 (2000).
Hamada et al., "Mesenchymal Stem Cells (MSC) as Therapeutic Cytoreagents for Gene Therapy," *Cancer Science* 96:149-156, (2005).
Haynesworth et al., "Cell-Based Tissue Engineering Therapies: The Influence of Whole Body Physiology," *Adv. Drug Deliv. Rev.* 33:3-14 (1998).
Horwitz et al., "Transplantability and Therapeutic Effects of Bone Marrow-Derived Mesenchymal Cells in Children with Osteogenesis," *Nature Medicine* 5:309-313 (1999).
Hu et al., "Abundant Progenitor Cells in the Adventitia Contribute to Atherosclerosis of Vein Grafts in ApoE-Deficient Mice," *J. Clin. Invest.* 113:1258-1265 (2004).
Karahuseyinoglu et al., "Functional Structure of Adipocytes Differentiated from Human Umbilical Cord Stroma-Derived Stem Cells," *Stem Cells* 26:682-691 (2008).
Kogler et al., "A New Human Somatic Stem Cell From Placental Cord Blood with Intrinsic Pluripotent Differentiation Potential," *J. Exp. Med.* 200(2):123-135 (2004).
Kulkarni et al., "Absence of Wharton's Jelly Around the Umbilical Arteries," *Indian J. Pediatr.* 74:87-89 (2007).
Li et al., "Mesenchymal Stem Cells Derived from Human Placenta Suppress Allogenic Umbilical Cord Blood Lymphocyte Proliferation," *Cell Research* 15:539-547 (2005).
Ma et al., "Human Umbilical Cord Wharton's Jelly-Derived Mesenchymal Stem Cells Differentiation into Nerve-Like Cells," *Chinese Medical Journal* 118:1987-1993 (2005).
Maccario et al., Interaction of Human Mesenchymal Stem Cells with Cells Involved in Alloantigen-Specific Immune Response Favors the Differentiation of CD4+ T-Cell Subsets Expression a Regulatory/Suppressive Phenotype, *Haematologica* 90:516-525 (2005).
Machaj et al., "Collection, In Vitro Expansion, and Freezing of Human Stem Cells of Fetal Origin," *Blood* Abstract #5268, 106:401B (2005).
Maitra et al., "Human Mesenchymal Stem Cells Support Unrelated Donor Hematopietic Stem Cells and Suppress T-Cell Activation," *Bone Marrow Transplantation* 33:597-604 (2004).
Minguell et al., "Mesenchymal Stem Cells," *Exp. Biol. Med.* 226:507-520 (2001).
Mitchell et al., "Matrix Cells from Wharton's Jelly Forms Neurons and Glia," *Stem Cells* 21:50-60 (2003).
Nanaev et al., "Stromal Differentiation and Architecture of the Human Umbilical Cord," *Placenta* 18:53-64 (1997).
Naughton et al., "Cells Isolated from Wharton's Jelly of the Human Umbilical Cord Develop a Cartilage Phenotype when Treated with TGFβ In Vitro," *Faseb Journal* 11:A19 (1997).

(56) References Cited

OTHER PUBLICATIONS

Parry et al., "Some Electron Microscope Observations on the Mesenchymal Structures of Full-Term Umbilical Cord," *Journal of Anatomy* 107:505-518 (1970).
Pegg et al., "Fractures in Cryopreserved Elastic Arteries," *Cryobiology* 34:183-192 (1997).
Pennati, "Biomechanical Properties of the Human Umbilical Cord," *Biorheology* 38:355-366 (2001).
Pereda et al., "New Advances in Human Embryology: Morphofunctional Relationship Between the Embryo and the Yolk Sac," *Medical Electron Microscopy* 35:67-78 (1999).
Romanov et al., "Searching for Alternative Sources of Postnatal Human Mesenchymal Stem Cells: Candidate MSC-Like Cells from Umbilical Cord," *Stem Cells* 21:105-110 (2003).
Sartore et al., "Contribution of Adventitial Fibroblast to Neointima Formation and Vascular Remodeling," *Circulation Research* 89:1111-1121 (2001).
Sarugaser et al., "Human Umbilical Cord Perivascular (HUCPV) Cells: A Source of Mesenchymal Progenitors," *Stem Cells* 23:200-229 (2005).
Sarugaser et al., "Human Umbilical Cord Perivascular (HUCPV) Cells: A Source of Cells for Allogeneic Cells Based Therapies," Podium Presentation—European Tissue Engineering Society, Lausanne, Switzerland (2004).
Sarugaser et al., "Human Umbilical Cord Wharton's Jelly as a Source of Mesenchymal Progenitors Capable of Expressing a Functional Osteogenic Phenotype," Podium Presentation—Orthopaedic Research Society, San Francisco, CA (2004).
Sarugaser et al., "Human Umbilical Cord Perivascular Cells as a Source of Mesenchymal Progenitors Capable of Expressing a Functional Osteogenic Phenotype," Poster Presentation—World Biomaterials Congress, Sydney, NSW, Australia (2004).
Sarugaser and Davies, "Human Umbilical Cord Wharton's Jelly as a Source of Mesenchymal Progenitors Capable of Expressing a Functional Osteogenic Phenotype," Podium Presentation—Tissue Engineering Society International Orlando, FL (2003).
Schoenberg et al., "Studies on Connective Tissue V, Feber Formation in Wharton's Jelly," *Laboratory Investigation* 9:350-355 (1960).
Sen et al., "Adipogenic Potential of Human Adipose Derived Stromal Cells from Multiple Donors is Heterogeneous," *J. Cell. Biochem.* 81:312-319 (2001).
Shi and Gronthos, "Perivascular Niche of Postnatal Mesenchymal Stem Cells in Human Bone Marrow and Dental Pulp," *J. Bone and Mineral Res.* 18:696-704 (2003).
Sotiropoulou et al., "Interactions Between Human Mesenchymal Stem Cells and Natural Killer Cells," *Stem Cells* 24:74-85 (2006).
Spaggiari et al., "Mesenchymal Stem Cell-Natural Killer Cell Interactions: Evidence that Activated NK Cells are Capable of Killing MSCs, Whereas MSCs Can Inhibit IL-2-Induced NK-Cell Proliferation," *Blood* 107:1484-1490 (2006).
Stenmark et al., "Hypoxic Activation of Advential Fibroblasts," *Chest* 122:326-334 (2002).
Takechi et al., "Ultrastructural and Immunohistochemical Studies of Wharton's Jelly Umbilical Cord Cells," *Placenta* 14:235-245 (1993).
Tuchmann-Duplessis et al., "Illustrated Human Embryology," Springer-Verlag (New York) 14-61 (1972).
Van Damme et al., "Bone Marrow Stromal Cells as Targets for Gene Therapy," *Current Gene Therapy* 2:195-209 (2002).
Wang et al., "Mesenchymal Stem Cells in the Wharton's Jelly of Human Umbilical Cord," *Stem Cells* 22:1330-1337 (2004).
Weiss, "Histology: Cell and Tissue Biology," Elseiver Biomedical (New York) 997-998 (1983).
Weiss et al., "Human Umbilical Cord Matrix Stem Cells: Preliminary Characterization and Effect of Transplantation in a Rodent Model of Parkinson's Disease," *Stem Cells* 24:781-792 (2006) (Supplemental tables and figures from web edition—17pages).
Wharton, "Adenographia," Oxford, UK, Oxford Univ. Press, 242-248 (1996).
International Search Report for Application No. PCT/CA2007/00781, completed Jun. 27, 2007.
International Search Report for International Application No. PCT/CA2009/000528 dated Jul. 28, 2009.
International Preliminary Report on Patentability (PCT/CA2009/000528) dated Oct. 26, 2010.
International Preliminary Report on Patentability for Application No. PCT/CA2007/00781, Issued on Nov. 11, 2008.
International Preliminary Report on Patentability for Application No. PCT/CA2006/002092, issued on Jun. 24, 2008.
Written Opinion of the International Search Authority for International Application No. PCT/CA2009/000528 dated Jul. 28, 2009.
Ennis et al., "In vitro immunologic properties of human umbilical cord perivascular cells," *Cytotherapy* 10:174-181 (2008).
Supplementary European Search Report for European Patent Application No. 09 734 792.6, dated Nov. 23, 2012.
Patocka et al., "Prophylaxis against nerve agent intoxications," Defense Science Journal. 56(5):775-784 (2006).
Reiser et al., "Potential of mesenchymal stem cells in gene therapy approaches for inherited and acquired diseases," Expert Opin Biol Ther. 5(12):1571-84 (2005).
Examination Report in Australian Patent Application No. 2009240738, issued Feb. 25, 2013 (4 pages).
Office Action in Japanese Patent Application No. 2011-505330, mailed Sep. 10, 2013 (4 pages).
Chilukuri et al., "Polyethylene glycosylation prolongs the circulatory stability of recombinant human butyrylcholinesterase," Chem Biol Interact. 157-8:115-21 (2005).
Office Action for Japanese Patent Application No. 2011-505330, mailed Aug. 22, 2014 (11 pages).

* cited by examiner

GENETICALLY MODIFIED HUMAN UMBILICAL CORD PERIVASCULAR CELLS FOR PROPHYLAXIS AGAINST OR TREATMENT OF BIOLOGICAL OR CHEMICAL AGENTS

CROSS-REFERENCE TO RELATED APPLICATIONS

This application claims priority under 35 U.S.C. §371 from international application PCT/CA2009/000528, filed Apr. 20, 2009, which claims benefit of U.S. Provisional Application No. 61/046,630, filed Apr. 21, 2008.

FIELD OF THE INVENTION

The invention provides methods of preventing or treating diseases or disorders caused by biological or chemical agents in a subject (e.g., a mammal, such as a human) by administering genetically modified human umbilical cord perivascular cells. Also provided are genetically modified human umbilical cord cells useful in such a method, and pharmaceutical compositions comprising them.

BACKGROUND OF THE INVENTION

Recombinant protein manufacturing for therapeutic proteins of clinical value has been a huge technical and commercial success of the biotechnology industry. Monoclonal antibodies (MAbs) had global sales in 2006 of $20.6 billion and are the fastest growing pharmaceutical segment. Six of the top selling US MAbs have sales over $1 billion annually with Rituxan® alone topping $4.7 billion in sales.

The utilization of MAbs for national defense is of keen interest to agencies mandated with the treatment of bioweapons casualties (and large scale epidemics of infectious diseases, e.g., SARS). Military and civilian research programs have identified several therapeutic MAbs and in some cases have begun the process of developing them as medical countermeasures for biological weapons.

Two issues must be addressed if MAbs are to be deployed as first line countermeasures: high drug cost and cumbersome delivery systems. The cost of manufacturing "biologics" is high. Recombinant proteins, like MAbs, are produced by a costly process involving large scale cGMP manufacturing and eukaryotic/prokaryotic fermentation systems, followed by downstream purification and polishing of the finished bulk pharmaceutical active. Secondly, the delivery of MAbs and other protein-based drugs via injection has been a therapeutic barrier. The large scale use of MAbs via conventional injection or infusion is impractical within the time and human resources constraints of a bioweapons attack on the battlefield or in a terrorist scenario.

SUMMARY OF THE INVENTION

The invention provides a method for protecting a subject against challenge from a biological or chemical agent by administering a human umbilical cord perivascular cell (HUCPVC) that has been genetically modified to increase the expression of an oligonucleotide or a polypeptide in the HUCPVC relative to a HUCPVC that has not been genetically modified. Also provided, in another aspect of the invention, are genetically modified HUCPVCs useful in such a method, and pharmaceutical compositions comprising such genetically modified cells.

The subject can be a vertebrate, such as a mammal (e.g., a human). The HUCPVC can be allogeneic or xenogeneic relative to the subject to whom it is administered.

In an embodiment of the invention, genetically modified HUCPVCs are administered to a subject to protect against challenge from a biological agent. The biological agent can be a pathogen, such as a bacterium, virus, fungus, or parasite. The bacterium can be *Pseudomonas aeruginosa, Salmonella typhimurium, Escherichia coli, Klebsiella pneumoniae, Bruscella, Burkholderia mallei, Yersinia pestis*, or *Bacillus anthracis*. The virus can be Gadgets Gully virus, Kadam virus, Kyasanur Forest disease virus, Langat virus, Omsk hemorrhagic fever virus, Powassan virus, Royal Farm virus, tick-borne encephalitis virus, Louping ill virus, Meaban virus, Saumarez Reef virus, Tyuleniy virus, Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, and Rio Bravo virus, Venezuelan equine encephalitis virus (VEE), Eastern equine encephalitis virus (EEE), Western equine encephalitis virus (WEE), Ebola virus, Marburg virus, smallpox virus, vaccinia virus, Lassa virus, Ippy virus, lymphocytic choriomeningitis virus (LCMV), Mobala virus, Mopeia virus, Amapari virus, Flexal virus, Guanarito virus, Junin virus, Latino virus, Machupo virus, Oliveros virus, Paraná virus, Pichinde virus, Pirital virus, Sabiá virus, Tacaribe virus, Tamiami virus, and Whitewater Arroyo virus, Sin Nombre virus, Hantaan virus, Rift Valley fever virus, Crimean-Congo hemorrhagic fever virus, Dugbe virus, herpes simplex virus (HSV), cytomegalovirus (CMV), Epstein-Barr virus (EBV), Kaposi's sarcoma associated-herpesvirus (KSHV), influenzavirus A, H5N1 avian influenza virus, influenzavirus B, influenzavirus C, severe acute respiratory syndrome (SARS) virus, rabies virus, or vesicular stomatitis virus (VSV). The fungus can be *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*. The parasite can be *Toxoplasma gondii, Plasmodium falciparum, P. vivax, P. ovale, P. malariae, Trypanosoma* spp., or *Legionella* spp.

In another embodiment of the invention, genetically modified HUCPVCs are administered to a subject to protect against challenge from a chemical agent. The chemical agent can be a bacterial, viral, fungal, or parasitic toxin, such as ricin, diphtheria toxin, *E. coli* enterotoxin, *Vibrio cholerae* enterotoxin, *Staphylococcal* enterotoxin, *Streptococcal* enterotoxin, or botulinum toxin. The chemical agent can be synthetically or naturally derived. The chemical agent can be a nerve agent, a vesicant, a blood agent, or a respiratory agent. The chemical agent can be a nitrogen mustard, sulfur mustard, acetylcholinesterase inhibitor, or Lewisite. The chemical can be saxitoxin, bis(2-chloroethyl)ethylamine, 2-chlorovinyldichloroarsine, 2-chloroethylchloromethylsulfide, bis (2-chloroethyl)sulfide, sarin (GB), cyclosarin (GF), soman (GD), tabun (GA), VX, amiton, PFIB, 3-quinuclidinyl benzilate, phosgene, diphosgene, cyanogens chloride, hydrogen cyanide, or chloropicrin.

In other embodiment of the invention, HUCPVCs are genetically modified to express a polypeptide, such as an antibody, an antibody fragment, a microbial antigen, a cytokine or growth factor, a hormone, a clotting factor, a drug resistance or anti-viral resistance polypeptide, an anti-venom agent, an antioxidant, a receptor or ligand, an immunomodulatory factor, a detectable label, or a cellular factor. The polypeptide can be endogenous or non-endogenous to the HUCPVC. In yet other embodiments, the HUCPVCs can be genetically modified to express two or more polypeptides. In still other embodiments, the HUCPVC can synthesize and secrete an antibody or antibody fragment; the antibody or antibody fragment can be recombinant, humanized, or monoclonal. The antibody or antibody fragment can be a single chain antibody (scFv), Fab, Fab'2, scFv, SMIP, diabody, nanobody, aptamer, or domain antibody. In yet other embodiments, the cytokine or growth factor can be tumor necrosis factor alpha (TNF-α), TNF-β, interferon-alpha (IFN-α), IFN-β, IFN-γ, interleukin 1 (IL-1), IL-1β, interleukin 2-14, granulocyte macrophage colony-stimulating factor (GM-CSF), granulocyte colony-stimulating factor (G-CSF), RANTES, MIP-1α), transforming growth factor-beta (TGF-β), platelet derived growth factor (PGDF), insulin-like growth factor (IGF), epidermal growth factor (EGF), vascular endothelial growth factor (VEGF), keratinocyte growth factor (KGF), erythropoietin (EPO), or thrombopoietin (TPO). The hormone can be angiotensinogen, angiotensin, parathyroid hormone (PTH), basic fibroblast growth factor-2, luteinizing hormone, follicle-stimulating hormone, adrenocorticotrophic hormone (ACTH), vasopressin, oxytocin, somatostatin, gastrin, cholecystokinin, leptin, atrial-natriuretic peptide, epinephrine, norephinephrine, dopamine, calcitonin, or insulin. The clotting factor can be factor VII, factor VIII, factor IX, or fibrinogen. The enzyme can be can be butyrylcholinesterase (BChE), adenosine deaminase, glucocerebrosidase, alpha-1 antitrypsin, a viral thymidine kinase, hypoxanthine phosphoribosyl transferase, manganese superoxide dismutase (Mn-SOD), catalase, copper-zinc-superoxide dismutase (CuZn-SOD), extracellular superoxide dismutase (EC-SOD), glutathione reductase, phenylalanine hydroxylase, nitric oxide synthetase, or paraoxinase. The receptor or ligand can be a T-cell receptor (TCR), LDL receptor, surface-bound immunoglobulin, soluble CD4, cystic fibrosis transmembrane conductance receptor (CFTR), or a $F_C$ receptor. The immunomodulatory factor can be CTLA-4, VCP, PLIF, LSF-1, Nip, CD200, uromodulin, CD40L (CD154), FasL, CD27L, CD30L, 4-1BBL, CD28, CD25, B7.1, B7.2, or OX40L. The detectable label can be green fluorescent protein (GFP). The cellular factor can be cytochrome b, ApoE, ApoC, ApoAI, MDR, tissue plasminogen activator (tPA), urokinase, hirudin, β-globin, α-globin, HbA, ras, src, or bd. The polypeptide can be a cellular protein that acts as an antigen, thereby generating an immune response in the subject against a biological or chemical agent.

In yet other embodiments of the invention, the HUCPVCs are genetically modified to express an oligonucleotide, e.g., an RNA interference (RNAi) molecule capable of inhibiting viral replication or infection. The RNAi molecule can be a small inhibitory RNA (siRNA) or short hairpin RNA (shRNA) molecule. The oligonucleotide can be endogenous or non-endogenous to the HUCPVC. In other embodiments, the HUCPVCs can be genetically modified to express two or more oligonucleotides.

In another embodiment of the invention, the subject has been exposed to a biological or chemical agent prior to receiving genetically modified HUCPVCs of the invention. The subject can be administered a single dose of HUCPVCs or multiple doses of HUCPVCs. The HUCPVCs can be administered as a vaccine to protect a subject in need thereof. The HUCPVC can be administered to a subject intravenously, intramuscularly, orally, by inhalation, parenterally, intraperitoneally, intraarterially, transdermally, sublingually, nasally, transbuccally, liposomally, adiposally, opthalmically, intraocularly, subcutaneously, intrathecally, topically, or locally. The subject can be administered between $10^1$ and $10^{13}$ HUCPVCs per dose, or between $10^3$ and $10^8$ HUCPVCs per dose.

In other embodiments of the invention, genetically modified HUCPVCs administered to a subject persist for greater than one week, one month, or two months. The HUCPVCs can evade immune recognition in the subject.

In yet other embodiments of the invention, genetically modified HUCPVCs are administered in combination with at least one mesenchymal stem cell (MSC) that is not a HUCPVC. The MSC can be genetically modified to increase the expression of an oligonucleotide or a polypeptide in the MSC relative to a MSC that has not been genetically modified. The MSC can be isolated from bone marrow, umbilical cord blood, embryonic yolk sac, placenta, skin, or blood. The MSCs can be genetically modified to express an oligonucleotide or polypeptide that is endogenous or non-endogenous to the HUCPVC.

In another embodiment of the invention, genetically modified HUCPVCs can be administered to a subject in combination with one or more therapeutic agents that enhance or prolong the prophylactic or therapeutic effect of HUCPVC treatment. The therapeutic agent can be, e.g., a cytokine, antiviral agent, immunostimulant, or immunosuppressant.

In yet another embodiment of the invention, genetically modified HUCPVCs are administered with a pharmaceutically acceptable carrier or excipient.

In another embodiment of the invention, genetically modified HUCPVCs are provided in a kit for administration to a subject in need of treatment of or protection from biological or chemical agents.

In general, the present invention provides for the use of HUCPVCs that are genetically modified for the preparation of a medicament for preventing or treating diseases or disorders caused by biological or chemical agents in a subject.

DEFINITIONS

The term "antibody" as used interchangeably herein, includes whole antibodies or immunoglobulins and any antigen-binding fragment or single chains thereof. Antibodies, as used herein, can be mammalian (e.g., human or mouse), humanized, chimeric, recombinant, synthetically produced, or naturally isolated. Antibodies of the present invention include all known forms of antibodies and other protein scaffolds with antibody-like properties. For example, the antibody can be a human antibody, a humanized antibody, a bispecific antibody, a chimeric antibody, or a protein scaffold with antibody-like properties, such as fibronectin or ankyrin repeats. The antibody also can be a Fab, Fab'2, scFv, SMIP, diabody, nanobody, aptamers, or a domain antibody. The antibody can have any of the following isotypes: IgG (e.g., IgG1, IgG2, IgG3, and IgG4), IgM, IgA (e.g., IgA1, IgA2, and IgAsec), IgD, or IgE.

The term "antibody fragment", as used herein, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include but are not limited to: (i) a Fab fragment, a monovalent fragment consisting of the $V_L$, $V_H$, $C_L$, and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., Nature 341:544-546 (1989)), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., Science 242:423-426 (1988) and Huston et al., Proc. Natl. Acad. Sci. USA 85:5879-5883 (1988)).

The terms "effective amount" or "amount effective to" or "therapeutically effective amount" means an amount of genetically modified HUCPVCs sufficient to produce a desired result, for example, preventing or treating a bacterial or viral infection, reducing a blood clot, or reversing the effects of a venom (e.g., snake venom).

By "genetically modified HUCPVC" is meant a human umbilical cord perivascular cell that recombinantly expresses at least one polypeptide (e.g., an antibody, cytokine, or hormone) or oligonucleotide (e.g., an siRNA) that, when administered to a human (e.g., a soldier), can prevent or treat diseases or disorders caused by pathogenic microbes or chemical agents (e.g., a toxin). This polypeptide or oligonucleotide will be recombinantly produced by the HUCPVC following transfer (e.g., transfection or transduction) of the genetic sequence for the polypeptide or oligonucleotide to the HUCPVC.

The term "human antibody," as used herein, is intended to include antibodies, or fragments thereof, having variable regions in which both the framework and CDR regions are derived from human germline immunoglobulin sequences as described, for example, by Kabat et al., (Sequences of proteins of Immunological Interest, Fifth Edition, U.S. Department of Health and Human Services, NIH Publication No. 91-3242 (1991)). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences (i.e., a humanized antibody or antibody fragment).

The term "humanized antibody" refers to any antibody or antibody fragment that includes at least one immunoglobulin domain having a variable region that includes a variable framework region substantially derived from a human immunoglobulin or antibody and complementarity determining regions (e.g., at least one CDR) substantially derived from a non-human immunoglobulin or antibody.

By "interferon" is meant a mammalian (e.g., a human) interferon-alpha, -beta, -gamma, or -tau polypeptide, or biologically-active fragment thereof, e.g., IFN-α (e.g., IFN-α-1a; see e.g., U.S. Patent Application No. 2007/0274950, incorporated by reference herein), IFN-α-1b, IFN-α-2a (see PCT Application No. WO 07/044083, incorporated by reference herein), and IFN-α-2b), IFN-α (e.g., described in U.S. Pat. No. 7,238,344, incorporated by reference herein; IFN-b-1a (AVONEX® and REBIF®), as described in U.S. Pat. No. 6,962,978, incorporated by reference herein, and IFN-β-1b (BETASERON®, as described in U.S. Pat. Nos. 4,588,585; 4,959,314; 4,737,462; and 4,450,103; incorporated by reference herein), IFN-g, and IFN-t (as described in U.S. Pat. No. 5,738,845 and U.S. Patent Application Publication Nos. 2004/0247565 and 2007/0243163; incorporated by reference herein).

By "pharmaceutically acceptable carrier" is meant a carrier which is physiologically acceptable to the treated subject (e.g., a human) while retaining the therapeutic properties of the genetically modified HUCPVCs with which it is administered. One exemplary pharmaceutically acceptable carrier is physiological saline. Other physiologically acceptable carriers and their formulations are known to one skilled in the art and described, for example, in Remington's Pharmaceutical Sciences, (18$^{th}$ edition), ed. A. Gennaro, 1990, Mack Publishing Company, Easton, Pa. incorporated herein by reference.

By "treating" is meant the reduction (e.g., by at least 10%, 15%, 20%, 25%, 30%, 35%, 40%, 45%, 50%, 60%, 70%, 80%, 90%, 95%, 99%, or even 100%) in the progression or severity of a disease or disorder (e.g., an infectious disease caused by a pathogenic microbe or toxin), or in the progression, severity, or frequency of one or more symptoms of the disease or disorder in a subject (e.g., a human).

DETAILED DESCRIPTION OF THE INVENTION

The invention provides genetically modified human umbilical cord perivascular cells (HUCPVCs), medically useful compositions comprising them, and the administration thereof to inhibit, reduce, prevent, or treat challenge by, e.g., a biological agent (e.g., infection by a pathogen, such as a bacteria, virus, fungus, and parasite) or a chemical agent (e.g., a biological or chemical (e.g., synthetic) toxin) in a vertebrate, e.g., a mammal, such as a human. In addition, genetically modified HUCPVCs can be administered prophylactically or therapeutically to a mammal likely to be exposed or exposed to, respectively, a pathogen or biological or chemical toxin, including those used in biological or chemical weapons. The methods of the present invention are particularly suited to the prophylaxis or treatment of a patient, e.g., military (e.g., a soldier), medical (e.g., a physician or nurse), or civilian personnel that are at heightened risk of exposure to biological or chemical weapons. Additionally, the invention provides for the prophylaxis or treatment of military or medical personnel that are stationed in regions of the world where indigenous infectious agents (e.g., malaria, flaviviruses e.g., dengue virus, West Nile virus, and yellow fever virus) present substantial health risks.

A HUCPVC can be genetically modified to express a polypeptide (e.g., a human polypeptide), such as an antibody, antibody fragment, cytokine, hormone, clotting factor, immunomodulatory factor, detectable label, or enzyme, that provides a prophylactic or therapeutic benefit to the treated subject (e.g., a human). In addition, a HUCPVC can be genetically modified to express an oligonucleotide (e.g., an RNAi molecule) that modulates (e.g., inhibits) a cellular process of the treated subject or a pathogenic microbe or toxin present therein. A HUCPVC can be genetically modified to express one or more therapeutic polypeptides or oligonucleotides for the prevention or treatment of one or more diseases or disorders that result from exposure to pathogenic microbes or toxins.

Genetically modified HUCPVCs can be co-administered with one or more diagnostic or therapeutic agents (e.g., an immunomodulatory agent such as interferon-alpha) to enhance or prolong the prophylactic or therapeutic qualities of the HUCPVC treatment. HUCPVCs can also be combined with one or more pharmaceutically acceptable carriers or excipients and can be formulated to be administered intravenously, intramuscularly, orally, by inhalation, parenterally, intraperitoneally, intraarterially, transdermally, sublingually, nasally, transbuccally, liposomally, adiposally, opthalmically, intraocularly, subcutaneously, intrathecally, topically, or locally. In a further aspect, the invention provides a kit, with instructions, for the prophylactic or therapeutic treatment of a mammal with one or more genetically modified HUCPVC populations.

Human Umbilical Cord Perivascular Cells (HUCPVCs)

Human umbilical cord perivascular cells (HUCPVCs) are a non-hematopoietic, mesenchymal, population of multipotent cells obtained from the perivascular region within the Wharton's Jelly of human umbilical cords (see, e.g., Sarugaser et al., "Human umbilical cord perivascular (HUCPV) cells: A source of mesenchymal progenitors," *Stem Cells* 23:220-229 (2005)). U.S. Patent Application Publication 2005/0148074 and International Patent Application Publication WO 2007/128115 describe methods for the isolation and in vitro culture of HUCPVCs, and are incorporated by reference herein. HUCPVCs are further characterized by relatively rapid proliferation, exhibiting a doubling time, in each of passages 2-7, of about 20 hours (serum dependent) when cultured under standard adherent conditions. Phenotypically, the HUCPVCs are characterized, at harvest, as Oct 4−, CD14−, CD19−, CD34−, CD44+, CD45−, CD49e+, CD90+, CD105(SH2)+, CD73(SH3)+, CD79b−, HLA-G−, CXCR4+, and c-kit+. In addition, HUCPVCs are positive for CK8, CK18, CK19, PD-L2, CD146 and 3G5 (a pericyte marker), at levels higher relative to cell populations extracted from Wharton's jelly sources other than the perivascular region.

Advantages of HUCPVCs

When used to recombinantly express a polypeptide or oligonucleotide (e.g., a human polypeptide or oligonucleotide), genetically modified HUCPVCs offer several advantages over other cell-based therapies. Because HUCPVCs exhibit low immunogenicity when administered to an allogeneic or xenogeneic host, they have an increased longevity within the host relative to other allogeneic or xenogeneic cells. HUCPVCs also have established gene expression modalities that result in therapeutically significant levels of a protein or oligonucleotide of interest (e.g., a recombinant polypeptide or oligonucleotide that the HUCPVC has been genetically modified to express). In addition, although HUCPVCs proliferate rapidly, they have a reduced risk of proliferative disorders relative to other cell-based gene therapy vehicles. Each of these advantageous properties of genetically modified HUCPVCs for the prophylaxis or treatment of a subject (e.g., a human) is discussed in detail below.

The low immunogenicity of genetically modified HUCPVCs make them ideal vehicles for administration to vertebrate subjects, e.g., mammals, such as humans, and particularly to allogeneic or xenogeneic recipients. HUCPVCs have been shown to have low immunogenicity based on their ability avoid detection by the host immune system (see, e.g., Sarugaser et al., (2005) and U.S. Patent Application Publication 2005/0148074). As such, HUCPVCs harvested from, e.g., a human (i.e., a donor) may be cultured in vitro and administered to another, un-related and HLA-mismatched, human (i.e., a host) without eliciting an allo-specific immune response in the host against the genetically modified HUCPVCs (see, e.g., Ennis et al., "In vitro immunologic properties of human umbilical cord perivascular cells" *Cytotherapy* 10(2):174-181 (2008)). Therefore, genetically modified HUCPVCs can be administered to heterologous human populations, or even to xenogeneic populations, without a loss of therapeutic efficacy due to activation of the host immune system. Furthermore, the ability to use HUCPVCs in virtually any vertebrate (e.g., a mammal, such as a human) allows for the large-scale preparation and storage (i.e., "stockpiling") for use during emergency situations (e.g., an infectious disease epidemic).

The low immunogencity of HUCPVCs results in increased longevity of these cells in vivo in the treated host relative to other allogeneic or xenogeneic cells. Similar mesenchymal cells have been documented to persist in a human host for years when delivered allogeneically (Le Blanc et al., "Fetal mesenchymal stem-cell engraftment in bone after in utero transplantation in a patient with severe osteogenesis imperfecta," *Transplantation* 79(11):1607-1614 (2005)), and thus, it can be expected that HUCPVCs will persist within a vertebrate (e.g., a mammalian, such as a human) host for at least weeks to months (e.g., 2 weeks, 4 weeks, 6 weeks, 2 months or more) following injection. The longevity of HUCPVCs used to provide polypeptides or oligonucleotides for therapy or prophylaxis (e.g., by providing a viral polypeptide or oligonucleotide) offers benefits over other techniques of vaccination or therapy. Whereas traditional vaccines or therapeutics require multiple administrations to confer a protective or therapeutic effect in an individual, a therapeutically-effective amount of genetically modified HUCPVCs can be administered to an individual in a single dose. Alternatively, two or more doses of the genetically modified HUCPVCs can be administered to provide prophylaxis or therapy. The longevity of genetically modified HUCPVCs used to prevent or treat diseases or disorders caused by microbial pathogens or toxins makes them especially useful for administration to military personnel (e.g., a soldier) who, due to the uncertain nature of military deployments, are not able to receive multiple administrations of a therapy or vaccine.

Another advantageous property of HUCPVCs is that they can be readily genetically modified by a number of standard transfection and transduction techniques to allow for the recombinant expression of a therapeutic polypeptide or oligonucleotide. As described further herein, genetic transfer can be achieved using viral vectors (e.g., adenoviruses and lentiviruses) and nucleic acid transfection (e.g., DNA plasmids in combination with liposomes, cationic vehicles, or electroporation).

Unlike many other mesenchymal stem cell populations that typically require the donation of bone marrow, HUCPVCs can be reliably collected from human umbilical cords that are normally discarded following birth. In industrialized nations, human umbilical cord blood products are now routinely collected and stored for possible future self or allo-transplantation. As such, the collection of HUCPVCs for expansion and genetic modification, according to the methods of the invention, are free of many of the logistical constraints associated with the collection of other mesenchymal stem cell populations.

Finally, HUCPVCs have a short population doubling time (see, e.g., Sarugaser et al., 2005) that allows for the rapid and large-scale preparation of genetically modified HUCPVCs for administration to a mammal (e.g., a human) in need thereof. HUCPVCs substantially lack the enzyme telomerase, and therefore the risk of developing proliferative diseases is minimal as these cells cannot divide more than a prescribed number of divisions before apoptosis occurs. In animal experiments, HUCPVCs are not known to generate tumors, even when administered in numbers orders of magnitude larger than clinically applicable.

Recombinant Polypeptide and Oligonucleotide Expression

In the present invention, HUCPVCs can be genetically modified to express one or more polypeptides (e.g., antibodies, cytokines, or hormones) or oligonucleotides (e.g., siRNA molecules) such that, when provided in a therapeutically-effective amount, the genetically modified HUCPVCs act as "stealth cells" to inhibit, reduce, prevent or treat challenge by a biological (e.g., a pathogenic microbe) or a chemical (e.g., a toxin) agent. Immunomodulatory oligonucleotides or polypeptides can also be expressed in HUCPVCs to modulate (e.g., increase or decrease) host immune responses. Polypeptides expressed in HUCPVCs can be secreted or displayed on the plasma membrane surface (e.g., a membrane-bound receptor or ligand). One or more oligonucleotides or polypeptides can be co-expressed in a single HUCPVC to allow for the treatment of or protection against one or more biological or chemical agents.

Antibodies and Antibody Fragments

The invention further provides for the expression of antibodies (e.g., humanized monoclonal antibodies) or antibody fragments by genetically modified HUCPVCs that specifically bind and neutralize pathogenic microbes or chemical agents (e.g., a toxin). As shown in Example 1, HUCPVCs that express an antibody or antibody fragment can be used to treat or protect a vertebrate (e.g., a mammal, such as a human (e.g., a soldier)) who has been exposed or is likely to be exposed, respectively, to a pathogenic microbe or chemical agent. Exemplary antibodies that can be used, for example, to modulate the immune system include TNF inhibitors (e.g., infliximab, adalimumab, certolizumab pegol), alemtuzumab, afelimomab, aselizumab, atlizumab, atorolimumab, basiliximab, belimumab, bertilimumab, cedelizumab, clenoliximab, daclizumab, dorlimomab aritox, dorlixizumab, eculizumab, efalizumab, elsilimomab, erlizumab, faralimomab, fontolizumab, galiximab, gantenerumab, gavilimomab, golimumab, gomiliximab, ibalizumab, inolimomab, ipilimumab, keliximab, lebrilizumab, lerdelimumab, lumiliximab, maslimomab, mepolizumab, metelimumab, morolimumab, muromonab-CD3, natalizumab, nerelimomab, ocrelizumab, odulimomab, omalizumab, otelixizumab, pascolizumab, pexelizumab, rituxumab, reslizumab, rovelizumab, ruplizumab, siplizumab, talizumab, telimomab aritox, tenelixmab, teplizumab, tocilizumab, toralizumab, vapaliximab, vepalimomab, visilizumab, zanolimumab, ziralimumab, and zolimomab aritox.

Microbial Antigens as Vaccines

HUCPVCs that express one or more antigens derived from a microbial pathogen (e.g., a bacteria, virus, fungus, or parasite) can be used as vaccines to elicit protective or therapeutic immune responses in the treated subject. Upon administration, genetically modified HUCPVCs express the microbial antigen that is recognized as foreign by the host immune system. The development of a primary immune response to the antigen, including the activation of the adaptive immune responses (e.g., host antibodies and T cells), allows for the creation of a potent and long-lived secondary response upon infection with the microbial pathogen. The use of bacterial, viral, fungal, and parasitic polypeptides in vaccines and the identification of immunogenic antigens derived from these microbes suitable for expression in a HUCPVC according to the methods of the invention are known in the art.

Cytokines and Growth Factors

The invention provides for the expression of cytokines and growth factors by genetically modified HUCPVCs. Many cytokines have immunomodulatory characteristics and can be used to augment immune responses or blunt immunopathological responses. Examples of cytokines and growth factors that can be expressed in HUCPVCs include, but are not limited to, tumor necrosis factor (TNF), such as TNF-α; interferons (e.g., interferon-α, interferon-β, and interferon-γ), interleukins (e.g., IL-1, IL-β, and interleukin 2-14), granulocyte macrophage colony-stimulating factor (GM-CSF), granulocyte colony-stimulating factor (G-CSF), chemokines (e.g., RANTES and MIP-1α), members of the transforming growth factor-beta (TGF-β) superfamily, platelet derived growth factor (PGDF), insulin-like growth factors (IGFs), epidermal growth factor (EGF), vascular endothelial growth factor (VEGF), keratinocyte growth factor (KGF), erythropoietin (EPO), and thrombopoietin (TPO).

Hormones

The invention provides for the expression of hormones by genetically modified HUCPVCs. Examples of hormones that can be expressed in HUCPVCs include, but are not limited to, angiotensinogen, angiotensin, parathyroid hormone (PTH), basic fibroblast growth factor-2, luteinizing hormone, follicle-stimulating hormone, adrenocorticotrophic hormone (ACTH), vasopressin, oxytocin, somatostatin, gastrin, cholecystokinin, leptin, atrial-natriuretic peptide, epinephrine, norephinephrine, dopamine, calcitonin, and insulin.

Blood Clotting Factors

The invention provides for the expression of blood clotting factors by genetically modified HUCPVCs. Examples of clotting factors that can be expressed in HUCPVCs include, but are not limited to, factors VII, VIII, and IX, and fibrinogen.

Enzymes

Examples of enzymes that can be expressed in HUCPVCs include, but are not limited to, butyrylcholinesterase (BChE), adenosine deaminase, glucocerebrosidase, alpha-1 antitrypsin, "suicide" polypeptides (e.g., a viral thymidine kinase (TK) e.g., a TK derived from herpes simplex virus, cytomegalovirus (CMV), or varicella-zoster virus), hypoxanthine phosphoribosyl transferase, antioxidants (e.g., manganese superoxide dismutase (Mn-SOD), catalase, copper-zinc-superoxide dismutase (CuZn-SOD), extracellular superoxide dismutase (EC-SOD), and glutathione reductase), phenylalanine hydroxylase, nitric oxide synthetase, and paraoxinase.

Immunomodulatory Factors

Examples of immunomodulatory factors that can be expressed in HUCPVCs include, but are not limited to, CTLA-4, VCP, PLIF, LSF-1, Nip, CD200, uromodulin, CD40L (CD154), FasL, CD27L, CD30L, 4-1BBL, CD28, CD25, B7.1, B7.2, and OX40L.

Receptors and Ligands

Examples of receptors and ligands that can be expressed in HUCPVCs include, but are not limited to, T-cell receptors (TCR), LDL receptors, surface-bound immunoglobulin, soluble CD4, cystic fibrosis transmembrane conductance receptor (CFTR), and $F_C$ receptors.

Detectable Labels

Detectable labels can be expressed in HUCPVCs to aid in the clinical application of these cells to a mammal (e.g., a human) in need thereof. A clinician can, for example, determine the quantity and longevity of labeled HUCPVCs that were administered to a patient by isolating a blood or tissue sample and analyzing for the presence of the detectable label. Detectable labels include fluorescent molecules such as green fluorescent protein (GFP).

Metabolites and Other Cellular Factors

Examples of metabolites and other factors that can be expressed in HUCPVCs include, but are not limited to, cytochrome b, cholesterol transport or metabolism polypeptides (e.g., ApoE, ApoC, ApoAI), drug resistance or anti-viral resistance polypeptides (e.g., MDR, ribozymes, antisense RNAs, anti-vital proteases), anti-venom agents, angiogenic peptides, tissue plasminogen activator (tPA), urinary plasminogen activator (e.g., urokinase), hirudin, vasoactive peptides, globins (e.g., β-globin, α-globin, HbA), protooncogenes (e.g., ras, src, and bcl), and secretory peptides (e.g., capable of acting as a competitive inhibitor of angiotensin converting enzyme, vascular smooth muscle calcium channel, or an adrenergic receptor).

RNA Interference

HUCPVCs can be genetically modified to express one or more RNA interference (RNAi) molecules when administered to a patient (e.g., a human). RNAi is a mechanism that inhibits gene expression by causing the degradation of specific RNA molecules or hindering the transcription of specific genes. Key to the mechanism of RNAi are small interfering RNA strands (siRNA), which have complementary nucleotide sequences to a targeted messenger RNA (mRNA) molecule. siRNAs are short, single-stranded nucleic acid molecule capable of inhibiting or down-regulating gene expression in a sequence-specific manner; see, for example, Zamore et al., Cell 101:25 33 (2000); Bass, Nature 411:428-429 (2001); Elbashir et al., Nature 411:494-498 (2001); and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. Methods of preparing a siRNA molecule for use in gene silencing are described in U.S. Pat. No. 7,078,196, which is hereby incorporated by reference.

The application of RNAi technology (e.g., an siRNA molecule) in the present invention can occur in several ways, each resulting in functional silencing of a gene product in a HUCPVC population. The functional silencing of one or more endogenous HUCPVC gene products may increase the longevity the HUCPVC in vivo (e.g., by silencing one or more pro-apoptotic gene products), or increase the expression of a therapeutic polypeptide (e.g., an antibody, cytokine, or hormone).

Functional gene silencing by an RNAi agent (e.g., an siRNA molecule) does not necessarily include complete inhibition of the targeted gene product. In some cases, marginal decreases in gene product expression caused by an RNAi agent can translate to significant functional or phenotypic changes in the host cell, tissue, organ, or animal. Therefore, gene silencing is understood to be a functional equivalent and the degree of gene product degradation to achieve silencing may differ between gene targets or host cell type. Gene silencing may decrease gene product expression by 1%, 2%, 3%, 4%, 5%, 6%, 7%, 8%, 9%, or 10%. Preferentially, gene product expression is decreased by 10%, 20%, 30%, 40%, 50%, 60%, 70%, 80%, 90%, or 100% (i.e., complete inhibition).

Genetic Modification of HUCPVCs

Recombinant expression of non-endogenous polypeptides or oligonucleotides in HUCPVCs can be accomplished by using several different standard gene transfer modalities. These modalities, their advantages and constraints, are discussed further below. Exemplary methods of genetically modifying HUCPVCs are also discussed in International Patent Application Publication WO 2007/128115, herein incorporated by reference.

Transduction (Viral Vectors)

Transduction is the infection of a target cell (e.g., a HUCPVC) by a virus that allows genetic modification of the target cell. Many viruses bind and infect mammalian cells and introduce their genetic material into the host cell as part of their replication cycle. Some types of viruses (e.g., retroviruses) integrate their viral genomes into the host's genome. This incorporates the genes of that virus among the genes of the host cell for the life span of that cell. In viruses modified for gene transfer, a donor gene (e.g., a humanized monoclonal antibody) is inserted into the viral genome. Additional modifications are made to the virus to improve infectivity or tropism (e.g., pseudotyping), reduce or eliminate replicative competency, and reduce immunogenicity. The newly-introduced mammalian gene will be expressed in the infected host cell or organism and, if replacing a defective host gene, can ameliorate conditions or diseases caused by the defective gene. Adenoviruses and retroviruses (including lentiviruses) are particularly attractive modalities for gene therapy applications, as discussed below, due to the ability to genetically-modify and exploit the life cycle of these viruses.

Adenoviruses

Recombinant adenoviral vectors offer several significant advantages for the expression of polypeptides (e.g., an antibodies, cytokines, or clotting factors) or oligonucleotides (e.g., an siRNA) in HUCPVCs. The viruses can be prepared at extremely high titer, infect non-replicating cells, and confer high-efficiency and high-level transduction of target cells in vivo after directed injection or perfusion. Furthermore, as adenoviruses do not integrate their DNA into the host genome, this gene therapy modality has a reduced risk of inducing spontaneous proliferative disorders. In animal models, adenoviral gene transfer has generally been found to mediate high-level expression for approximately one week. The duration of transgene expression may be prolonged, and ectopic expression reduced, by using tissue-specific promoters. Other improvements in the molecular engineering of the adenoviral vector itself have produced more sustained transgene expression and less inflammation. This is seen with so-called "second generation" vectors harboring specific mutations in additional early adenoviral genes and "gutless" vectors in which virtually all the viral genes are deleted utilizing a cre-lox strategy (Engelhardt et al., Proc. Natl. Acad. Sci. USA 91:6196-6200 (1994) and Kochanek et al., Proc. Natl. Acad. Sci. USA 93:5731-5736 (1996)). In addition, recombinant adeno-associated viruses (rAAV), derived from non-pathogenic parvoviruses, can be used to express a polypeptide or oligonucleotide as these vectors evoke almost no cellular immune response, and produce transgene expression lasting months in most systems. Incorporation of a tissue-specific promoter is, again, beneficial.

Retroviruses

Other viral vectors useful for the delivery of polypeptides or oligonucleotides into a subject or cells are retroviruses, including lentiviruses. As opposed to adenoviruses, the genetic material in retroviruses is in the form of RNA molecules, while the genetic material of their hosts is in the form of DNA. When a retrovirus infects a host cell, it will introduce its RNA together with some enzymes into the cell. This RNA molecule from the retrovirus will produce a double-stranded DNA copy (provirus) from its RNA molecules through a process called reverse transcription. Following transport into the cell nucleus, the proviral DNA is integrated in a host chromosome, permanently altering the genome of the infected cell and any progeny cells that may arise. The ability to permanently introduce a gene encoding a polypeptide or oligonucleotide into a cell such as a HUCPVC is the defining characteristic of retroviruses used for gene therapy. Retroviruses include lentiviruses, a family of viruses including human immunodeficiency virus (HIV) that includes several accessory proteins to facilitate viral infection and proviral integration.

One problem with using retroviruses for gene therapy is that the integrase enzyme can insert the genetic material of the virus in any arbitrary position in the genome of the host. If genetic material happens to be inserted in the middle of one of the original genes of the host cell, this gene will be disrupted (e.g., insertional mutagenesis). If the gene happens to be one regulating cell division, uncontrolled cell division (e.g., cancer) can occur. This problem has recently begun to be addressed by utilizing zinc finger nucleases or by including certain sequences such as the beta-globin locus control region to direct the site of integration to specific chromosomal sites. Despite this consideration, retroviruses and lentiviruses have considerable utility for gene therapy applications. Current, "third-generation" lentiviral vectors feature total replication incompetence, broad tropism, and increased gene transfer capacity for mammalian cells (see Mangeat, B. and Trono, D., "Lentiviral vectors and antiretroviral intrinsic immunity," *Human Gene Therapy* 16(8):913-920 (2005) and Wiznerowicz, M. and Trono, D., "Harnessing HIV for therapy, basic research and biotechnology," *Trends Biotechnol.* 23(1):42-7 (2005)). Lentiviruses pseudotyped with, e.g., vesicular stomatitis virus glycoprotein (VSV-G) or feline endogenous virus RD114 envelope glycoprotein can be used to transduce HUCPVCs (see, e.g., Zhang et al., "Transduction of bone-marrow-derived mesenchymal stem cells by using lentivirus vectors pseudotyped with modified RD 114 envelope glycoproteins," *J. Virol.* 78(3):1219-1229 (2004)). U.S. Pat. Nos. 5,919,458, 5,994,136, and 7,198,950, hereby incorporated by reference, describe the production and use of lentiviruses to genetically modify target cells.

Other Viral Vectors

Besides adenoviral and retroviral vectors, other viral vectors and techniques are known in the art that can be used to transfer a DNA vector (e.g., a plasmid) encoding a desired polypeptide or oligonucleotide into a subject or cells. These include, e.g., those described by Wattanapitayakul and Bauer (*Biomed. Pharmacother* 54:487-504 (2000), and citations therein.

Transfection
Naked DNA and Oligonucleotides

Naked DNA or oligonucleotides (e.g., DNA vectors such as plasmids) encoding polypeptides (e.g., an antibody, cytokine, or hormone) or RNA interference molecule (e.g., an siRNA or shRNA) can also be used to genetically modify HUCPVCs. This is the simplest method of non-viral transfection. Clinical trials carried out using intramuscular injection of a naked DNA plasmid have had some success; however expression has been low in comparison to other methods of transfection. Other efficient methods for delivery of naked DNA exist such as electroporation and the use of a "gene gun," which shoots DNA-coated gold particles into the cell using high pressure gas.

Lipoplexes and Polyplexes

To improve the delivery of a DNA vector (e.g., a plasmid) into a HUCPVC, the DNA can be protected from damage and its entry into the cell facilitated. Lipoplexes and polyplexes have the ability to protect transfer DNA from undesirable degradation during the transfection process. Plasmid DNA can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge they interact with the cell membrane, endocytosis of the lipoplex occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Hybrid Methods

Due to every method of gene transfer having shortcomings, there have been some hybrid methods developed that combine two or more techniques. Virosomes, for example, combine liposomes with an inactivated virus. This approach has been shown to result in more efficient gene transfer in respiratory epithelial cells than either viral or liposomal methods alone. Other methods involve mixing other viral vectors with cationic lipids or hybridising viruses. Each of these methods can be used to facilitate transfer of a DNA vector (e.g., a plasmid) into a HUCPVC.

Dendrimers

Dendrimers may be also be used to genetically modify HUCPVCs. A dendrimer is a highly branched macromolecule with a spherical shape. The surface of the particle may be functionalized in many ways, and many of the properties of the resulting construct are determined by its surface. In particular it is possible to construct a cationic dendrimer (i.e., one with a positive surface charge). When in the presence of genetic material such as a DNA plasmid, charge complimentarity leads to a temporary association of the nucleic acid with the cationic dendrimer. On reaching its destination the dendrimer-nucleic acid complex is then taken into the HUCPVC via endocytosis.

Biological and Chemical Agents

The methods of the invention provide for the administration of genetically modified HUCPVCs to a subject (e.g., humans, such as military personnel) who have been exposed or are at increased risk of exposure to biological or chemical agents.

Bacteria

The methods of the invention can be used to treat or prevent a bacterial infection in a subject (e.g., a human). Bacteria that cause human disease or sickness include, but are not limited to, *Pseudomonas aeruginosa, Salmonella typhimurium, Escherichia coli, Klebsiella pneumoniae, Bruscella, Burkholderia mallei, Yersinia pestis*, and *Bacillus anthracis*.

Viruses

The methods of the invention can be used to treat or prevent a viral infection in a subject (e.g., a human). Viruses that cause human disease or sickness include, but are not restricted to: Flaviviruses (e.g., Gadgets Gully virus, Kadam virus, Kyasanur Forest disease virus, Langat virus, Omsk hemorrhagic fever virus, Powassan virus, Royal Farm virus, tick-borne encephalitis virus, Louping ill virus, Meaban virus, Saumarez Reef virus, Tyuleniy virus, Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, and Rio Bravo virus), Togaviruses (e.g., Venezuelan equine encephalitis virus (VEE), Eastern equine encephalitis virus (EEE), and Western equine encephalitis virus (WEE)), Filoviruses (e.g., Ebola virus (e.g., Ivory Coast, Reston, Sudan, Uganda, and Zaire strains), Marburg virus (e.g., Angola, Ci67, Musoke, Popp, and Ravn strains)), Poxviruses (e.g., smallpox virus, vaccinia virus), Arenaviruses (e.g., Lassa virus (e.g., Josiah, LP, and GA391 strains), Ippy virus, lymphocytic choriomeningitis virus, Mobala virus, Mopeia virus, Amapari virus, Flexal virus, Guanarito virus, Junin virus, Latino virus, Machupo virus, Oliveros virus, Paraná virus, Pichinde virus, Pirital virus, Sabiá virus, Tacaribe virus, Tamiami virus, and Whitewater Arroyo virus), Bunyaviruses (e.g., Sin Nombre virus, Hantaan virus, Rift Valley fever virus, Crimean-Congo hemorrhagic fever virus, and nairoviruses (e.g., Dugbe virus)), Herpesviruses (e.g., herpes simplex virus (HSV), cytomegalovirus (CMV), Epstein-Barr virus (EBV), and Kaposi's sarcoma associated-herpesvirus (KSHV), Orthomyxoviruses (e.g., influenza viruses such as influenzaviruses A (e.g., H5N1 avian influenza), B, and C), Coronaviruses (e.g., severe acute respiratory syndrome (SARS) virus), and Rhabdoviruses (e.g., rabies virus and vesicular stomatitis virus (VSV)).

Fungi

The methods of the invention can be used to treat or prevent fungal infections in a subject (e.g., a human). Fungi that cause human disease or sickness include, but are not limited to, *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii*, and *Zygomycetes* (e.g., *Absidia corymbifera, Rhizomucor pusillus*, and *Rhizopus arrhizus*)

Parasites

The methods of the invention can be used to treat or prevent a parasitic infection in a subject (e.g., a human). Parasites that cause human disease or sickness include, but are not restricted to, *Toxoplasma gondii, Plasmodium* (*falciparum, vivax, ovale*, and *malariae*), *Trypanosoma* spp., and *Legionella* spp.

Chemical Agents (Toxins)

The methods of the invention can be used to treat or prevent diseases, symptoms, or conditions caused by exposure of a mammal (e.g., a human) to a chemical agent (e.g., a toxin, chemical weapon, or vesicant). Chemical agents that cause mammalian disease or sickness include, but are not limited to, ricin, diphtheria toxin, *Escherichia coli* enterotoxin, *Vibrio cholerae* enterotoxin, *Staphylococcal* enterotoxin, *Streptococcal* enterotoxin, botulinum toxin, saxitoxin, nitrogen mustards (e.g., bis(2-chloroethyl)ethylamine), Lewisites (e.g., 2-chlorovinyldichloroarsine), sulfur mustards (e.g., 2-chloroethylchloromethylsulfide and bis(2-chloroethyl)sulfide), sarin (GB; O-isopropyl methylphosphonofluoridate), cyclosarin (GF), soman (GD; O-pinacolyl methylphosphonofluoridate), tabun (GA; O-ethyl, n,n-dimethylphosphoramidocyanidate), VX (O-ethyl S-2-diisopropylaminoethyl methylphosphonothiolate), amiton, PFIB, 3-quinuclidinyl benzilate, phosgene, diphosgene, cyanogens chloride, hydrogen cyanide, chloropicrin, and acetylcholinesterase inhibitors (e.g., Novichok agents).

Subjects that can be Treated with the Genetically Modified HUCPVCs of the Invention Subjects that can benefit from the administration of genetically modified HUCPVCs, according to the methods of the invention, to treat, inhibit, reduce, or prevent a challenge with a biological or chemical agent, such as a pathogen or toxin. These subjects include, e.g., vertebrates, such as birds (e.g., poultry such as chickens, turkeys, geese, ducks, grouse, swans, peacocks, pigeons, doves, and pheasants), reptiles (e.g., snakes and lizards), amphibians (e.g., frogs and salamanders), mammals (e.g., humans, non-human primates (e.g., monkeys, chimpanzees, apes), ungulates (e.g., horses, cows, goats, pigs, sheep, donkeys, and deer), dogs, and cats.

Dosing and Administration

The present invention provides genetically modified HUCPVCs that express in a therapeutically effective amount one or more polypeptides (e.g., antibodies, cytokines, or hormones) or oligonucleotides (e.g., siRNAs). Genetically modified HUCPVCs are intended for parenteral (e.g., intramuscular, sub-cutaneous, and intravenous), intranasal, topical, oral, or local administration, such as by a transdermal means, for prophylactic or therapeutic treatment. Commonly, the genetically modified HUCPVCs are administered parenterally (e.g., by intravenous, intramuscular, or subcutaneous injection) or intraarticular injection at areas affected by the condition. Additional routes of administration include intravascular, intra-arterial, intraperitoneal, intraventricular, intraepidural, as well as nasal, ophthalmic, intrascleral, intraorbital, rectal, topical, or aerosol inhalation administration.

Genetically modified HUCPVCs can be administered for prophylactic or therapeutic treatments. In prophylactic applications, genetically modified HUCPVCs are administered to a subject (e.g., a human) with a clinically determined predisposition or increased susceptibility to a challenge with a pathogen or chemical agent (e.g., a chemical agent). For example, HUCPVCs that have been genetically modified to express butyrylcholinesterase (BChE) can be administered to a subject (e.g., a soldier) who is homozygous recessive for the BChE gene to treat or prevent challenge with a chemical agent because the BChE polypeptide, which is expressed in the genetically modified HUCPVCs, can metabolize several chemical agents.

Genetically modified HUCPVCs can be administered to the subject (e.g., a human) in an amount sufficient to delay, reduce, or preferably prevent the onset of clinical disease caused by challenge with a microbial pathogen or chemical agent. In therapeutic applications, genetically modified HUCPVCs are administered to a subject (e.g., a soldier) already suffering from infection by a microbial pathogen or exposure to a chemical agent in an amount sufficient to cure or at least partially arrest the symptoms of these agents. The number of HUCPVCs adequate to accomplish this purpose is defined as a "therapeutically effective dose." Amounts effective for this use may depend on the severity of the disease or condition and the weight and general state of the patient. The total number of genetically modified HUCPVCs administered to a subject in single or multiple doses according to the methods of the invention can be e.g., $10^1$, $10^2$, $10^3$, $10^4$, $10^5$, $10^6$, $10^7$, $10^8$, $10^9$, or more cells, although an effective dose will probably lie in the range of $10^3$ to $10^7$ cells per dose. Preferably, the genetically modified HUCPVCs are administered to the subject in need thereof in a single dose. Genetically modified HUCPVCs can also be applied as an initial dose followed by booster administrations at one or more hourly, daily, weekly, monthly, or bimonthly intervals. The total effective dose of genetically modified HUCPVCs administered to a subject as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month, or once every two months). Alternatively, continuous intravenous infusions sufficient to maintain therapeutically effective concentrations in the blood are contemplated.

The therapeutically-effective amount of a genetically modified HUCPVC to be administered to a subject (e.g., a human) according to the methods of the invention can be determined by a skilled artisan. Factors that can be considered include, e.g., individual differences in the subject's age, weight, condition (e.g., the type of agent to which the subject has been or may be exposed, the severity of the effect of the biological or chemical agent (e.g., a pathogenic infection or toxin) on the subject), and level of exposure to a biological or chemical agent. Exposure to a biological or chemical agent can be determined using well characterized physiological markers (see, e.g., Black and Nort, "Biological Markers of Exposure to Chemical Warfare Agents" in Chemical Warfare Agents, Second Edition (Second Edition), John Wiley & Sons, Ltd., 2007, which is incorporated by reference herein in its entirety).

The invention provides for the co-administration of a second genetically modified HUCPVC population to a subject (e.g., a human), in which the second HUCPVC population expresses one or more different polypeptides or oligonucleotides for prophylactic or therapeutic applications. Alternatively, one or more mesenchymal stem cells (MSC) that are not HUCPVCs can be administered. In this case, the MSC can be genetically modified to express a polypeptide or oligonucleotide. It is not always necessary, however, to administer both HUCPVC or MSC populations at the same time or in the same way. In some cases, the administration of the second population may begin shortly after the completion of the administration period for the first population or vice versa. Such time gap between the two administration periods may vary from one day to one week, to one month, or more. In some cases, two genetically modified HUCPVC populations can be co-administered initially, and subsequently administered singly in following periods (e.g., the administration of two or more HUCPVC populations that individually express a single monoclonal antibody that is protective against a certain viral serotype or strain). In addition HUCPVC populations can be modified to express more than one polypeptide or oligonucleotide for prophylactic or therapeutic applications, thus removing the need for multiple administrations.

Single or multiple (e.g., 2, 3, 4, 5, 6, 7, 8, 9, 10, 15, 20 or more) administrations of the compositions of the invention that include an effective amount can be carried out with dose levels and pattern being selected by the treating clinician (e.g., a physician or veterinarian). The dose and administration schedule can be determined and adjusted based on the severity or likelihood of exposure to an infectious microbe or chemical agent. Furthermore, a subject (e.g., a mammal, such as a human (e.g., a soldier)) administered genetically modified HUCPVCs can be monitored throughout the course of treatment according to the methods commonly practiced by clinicians or those described herein.

One or more physiologically acceptable excipients or carriers can also be included in the compositions for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, Langer, *Science* 249:1527-1533, 1990.

Additional Therapeutic Regimens

The invention provides for the co-administration of one or more therapeutic agents (e.g., anti-microbial agents, such as anti-viral compounds) in combination with genetically modified HUCPVCs. For example, an additional therapeutic agent may be administered with genetically modified HUCPVCs described herein at concentrations known to be effective for such therapeutic agents. Particularly useful therapeutic agents include, e.g., cytokines, antiviral agents, immunostimulants, immunosuppresants, and immunization vaccines.

In some instances, the genetically modified HUCPVCs and the additional therapeutic agents are administered at least one hour, two hours, four hours, six hours, 10 hours, 12 hours, 18 hours, 24 hours, three days, seven days, fourteen days, or one month apart. The dosage and frequency of administration of each component can be controlled independently. The additional therapeutic agents described herein may be admixed with additional active or inert ingredients, e.g., in conventional pharmaceutically acceptable carriers. A pharmaceutical carrier can be any compatible, non-toxic substance suitable for the administration of the compositions of the present invention to a subject. Pharmaceutically acceptable carriers include, for example, water, saline, buffers and other compounds, described, for example, in the Merck Index, Merck & Co., Rahway, N.J. A slow release formulation or a slow release apparatus may be also be used for continuous administration. The additional therapeutic regimen may involve other therapies, including modification to the lifestyle of the subject being treated.

Cytokines

Cytokines can be used as an additional therapeutic agent, either in combination with genetically modified HUCPVCs. Exemplary cytokines are IL-1, IL-2, IL-3, IL-4, IL-5, IL-6, IL-7, IL-9, IL-10, IL-11, IL-12, IL-13, G-CSF, IL-15, GM-CSF, OSM, LIF, IFN-γ, IFN-α, IFN-β, TNF-α, TNF-β, LT-β, IL-8, MCP-1, MIP-α, MIP-β, RANTES, TGF-β, IL-1α, IL-1β, IL-1 RA, and MIF.

Antiviral Agents

Antiviral agents can be used as an additional therapeutic agent, either in combination with genetically modified HUCPVCs or in a separate administration. Exemplary antiviral agents are abacavir, aciclovir, acyclovir, adefovir, amantadine, amprenavir, arbidol, atazanavir, atripla, brivudine, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, gardasil, ibacitabine, imunovir, idoxuridine, imiquimod, indinavir, inosine, integrase inhibitors, interferon type III, interferon type II, interferon type I, interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine. Exemplary antiviral agents are listed in, e.g., U.S. Pat. Nos. 6,093,550 and 6,894,033, hereby incorporated by reference.

Immunostimulants

Immunogenicity of the pharmaceutical composition may be significantly improved if the composition of the present invention is co-administered with an immunostimulatory agent or adjuvant. Exemplary immunostimulants include aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof. Other molecules that can stimulate or co-stimulate cells of the immune system include CD40L (CD154), FasL, CD27L, CD30L, 4-1BBL, CD28, CD25, B7.1, B7.2, and OX40L.

Immunosuppressants

It may be desirable to suppress the immune system of a treated individual to prevent e.g., immunopathology associated with an infection (e.g., dengue hemorrhagic fever syndrome) or to reduce inflammation associated with exposure to a toxin. Immunosuppressants can also be used to decrease host rejection of administered HUCPVCs, thereby increasing the longevity of these cells in vivo. Exemplary immunosuppressants include abetimus, deforolimus, everolimus, gusperimus, pimecrolimus, sirolimus, tacrolimus, temsirolimus, anakinra, azathioprine, ciclosporin, leflunomide, methotrexate, mycophenolic acid, and thalidomide. Many monoclonal antibodies that cause immunosuppression are also known in the art, including TNF inhibitors (e.g., infliximab, adalimumab, certolizumab pegol), alemtuzumab, afelimomab, aselizumab, atlizumab, atorolimumab, basiliximab, belimumab, bertilimumab, cedelizumab, clenoliximab, daclizumab, dorlimomab aritox, dorlixizumab, eculizumab, efalizumab, elsilimomab, erlizumab, faralimomab, fontolizumab, galiximab, gantenerumab, gavilimomab, golimumab, gomiliximab, ibalizumab, inolimomab, ipilimumab, keliximab, lebrilizumab, lerdelimumab, lumiliximab, maslimomab, mepolizumab, metelimumab, morolimumab, muromonab-CD3, natalizumab, nerelimomab, ocrelizumab, odulimomab, omalizumab, otelixizumab, pascolizumab, pexelizumab, rituximab, reslizumab, rovelizumab, ruplizumab, siplizumab, talizumab, telimomab aritox, teneliximab, teplizumab, tocilizumab, toralizumab, vapaliximab, vepalimomab, visilizumab, zanolimumab, ziralimumab, and zolimomab aritox.

EXAMPLES

The following examples are to illustrate the invention. They are not meant to limit the invention in any way.

Example 1

HUCPVCs that Express a Humanized Monoclonal Antibody Against the Venezuelan Equine Encephalitis Virus (VEEV) E2 Antigen History of VEEV as a Biological Weapons Agent All three equine encephalitis fevers, Venezuelan equine encephalitis (VEE), Western equine encephalitis (WEE), and Eastern equine encephalitis (EEE), are potential biological weapons agents. Venezuelan equine encephalitis virus (VEEV) is a particularly appealing agent for use in a weapon due to its infectious capacity (only 10-100 virions are needed to infect a person) and effectiveness as an incapacitating agent. VEEV infections are rarely fatal but cause severe symptoms similar to influenza and hence can be difficult to diagnose. Encephalitis fevers cause inflammation of the brain and long-term side effects such as nervous system damage. A potential biological attack using VEEV would be through the aerosolized route, but would be most effective during periods when mosquitoes are most active as VEEV is an arbovirus. VEEV can also be disseminated in a stable liquid or dried form.

The United States weaponized VEEV was an offensive incapacitating agent before the termination of its biological weapons program. The Soviet Union also weaponized VEEV as an incapacitating agent. Soviet scientists also experimented with splicing the VEEV genome into smallpox viruses. The results were a recombinant smallpox-VEE chimera virus that resembled smallpox under a microscope but produced different symptoms in its hosts. In 1959, a freeze-dried vial containing VEEV was accidentally dropped by Soviet medical personnel and 20 laboratory staff became infected. This laboratory accident and other naturally occurring outbreaks of VEEV demonstrate the infectiousness of aerosolized VEEV.

Genetic Payload: Humanized Anti-E2/VEEV Antibodies

A recombinant gene fusion (pRSmA116huFc) was produced that encoded a human $IgG_1$ heavy chain constant region and a single chain fragment variable antibody of 1A4A1 (Hu et al., "Humanization and mammalian expression of a murine monoclonal antibody against Venezuelan equine encephalitis virus," Vaccine 25:3210-3214 (2007)). The murine monoclonal antibody 1A4A1 has been shown to recognize a conserved neutralizing epitope of envelope glycoprotein E2 of VEEV (Roehrig et al., "The neutralizing site on the E2 glycoprotein of Venezuelan equine encephalomyelitis (TC085) virus is composed of multiple conformationally stable epitopes," Virology 142:347-356 (1985)). This gene fusion was placed under the transcriptional control of an adeno-associated virus (AAV) to drive high level constitutive expression in human cells.

In Vitro Evaluation of Anti-E2 VEEV Recombinant Antibody Production

HUCPVCs are cultured (see, e.g., Ennis et al., (2008)) and transduced with pAAV-RsmA116huFc to allow expression of the monoclonal antibody 1A4A1. Further experiments (e.g., ELISA) will confirm the quantity of recombinant antibody that the genetically modified HUCPVCs can produce and describe the longevity of this expression. Additionally, binding studies will be conducted to confirm the biological activity of the recombinant antibodies and their ability to neutralize VEEV virions.

In Vivo Antibody Production, Pharmacokinetics and Efficacy

Stable HUCPVC transfectants shown to secrete biologically active anti-VEEV antibodies will be introduced into mice by i.v., i.m., or subcutaneous administration. Immunocompetent mice will be used as biologically similar cells from marrow stroma are not rejected when used xenogeneically in vivo (Plotnikov et al., "Xenografted adult human mesenchymal stem cells provide a platform for sustained biological pacemaker function in canine heart" Circulation 116:706-713 (2007)), and preliminary work with HUCPVCs in rats does not show rejection (unpublished data). Sequential serum samples will be evaluated for the quantity, quality, and longevity of anti-VEEV antibody.

Pathogen Challenge Experiments

Once therapeutic levels of anti-VEEV MAb are confirmed in treated mice, the mice will be challenged with an intranasal VEEV challenge to measure the protective effect of the expressed MAb using standard methods.

Example 2

HUCPVCs that Express the Ebola Virus Glycoprotein (GP) to Stimulate a Protective Immune Response Genetic Payload: Glycoprotein of Ebola virus (Zaire Strain)

An rVSV vector expressing the glycoprotein (GP) of Zaire ebolavirus strain Mayinga (ZEBOV) is generated (see, e.g., Garbutt et al., *J Virol.* 78: 5458-65, 2004, and Jones et al., *Nat Med* 11: 786-90, 2005). Specifically, a plasmid containing five VSV genes (nucleoprotein (N), phosphoprotein (P), matrix protein (M), glycoprotein (G), and polymerase (L)), flanked by the bacteriophage T7 promoter sequence, the VSV leader sequence, the hepatitis virus delta virus ribozyme sequence, and the T7 terminator sequence is employed. Between the G and L genes, a unique linker site (Xho-NheI) is present, flanked by a transcriptional start and stop signal for the Ebola virus glycoprotein to be expressed. Cultured HUCPVCs are transduced with the pVSV/Ebola GP vector at various multiplicities of infection.

In Vitro Evaluation of Glycoprotein Production and Antigenicity

Transduced HUCPVCs are tested for Ebola GP expression using standard immunobloting analysis, such as ELISA, Western blot, dot blot, or immunoprecipitation.

Mixed lymphocyte reactions, lymphoproliferative assays, and cytotoxicity assays (e.g., chromium release or IFN-gamma ELISPOT) are used to determine the antigenicity of the expressed Ebola GP when used to stimulate lymphocytes in culture.

In Vivo Glycoprotein Production, Pharmacokinetics and Efficacy

Upon in vitro confirmation of GP expression and antigenicity, cultured HUCPVCs are administered to mice intravenously and intraperitoneally to prime anti-GP immunity. At one week intervals following immunization, mice are sacrificed and the spleen and lymph nodes (e.g., axillary, inguinal, and brachial) are harvested. Lymphoproliferative and cytotoxicity assays, as described above, are used to determine the breadth and efficacy of the adaptive anti-GP immune response (e.g., T cells and neutralizing antibodies).

Example 3

HUCPVCs that Express Interferons to Provide Broad Spectrum Protection Against Many Different Viruses The recombinant expression of interferons in HUCPVCs that are administered to a patient (e.g., a soldier) can provide broad spectrum protection against many different viruses (e.g., hemorrhagic fever viruses). Interferons (IFNs) produced by genetically modified HUCPVCs can be used prophylactically or therapeutically by patients exposed to or infected with pathogenic viruses. When administered as a therapeutic, IFNs exhibit a short in vivo half-life. Administration of HUCPVCs genetically modified to express one or more IFNs (e.g., IFN-alpha) overcomes this shortcoming by providing extended release and delivery of the IFN. Standard clinical administration of IFNs requires frequent injections or modification (e.g., pegylation) due to the rapid decay kinetics of IFN. In the present example, this problem is overcome by providing IFN-alpha using a genetically modified HUCPVC.

Genetic Payload: Interferon Alpha (IFN-α)

HUCPVCs are transduced with a retroviral vector (e.g., a lentivirus) that encodes interferon-alpha. Upon integration of the proviral DNA into the HUCPVC chromosome, a constitutively active promoter (e.g., a CMV promoter) is used to drive expression and secretion of the IFN-α.

In Vitro Evaluation of IFN-α Production

Transduced HUCPVCs are tested for IFN-α expression using standard immunobloting analysis, such as ELISA, Western blot, dot blot, or immunoprecipitation IFN-α activity is confirmed by antiproliferative assays as described by Foser et al., "Improved biological and transcriptional activity of monopegylated interferon-alpha-2a isomers," *The Pharmacogenomics Jour.* 3:312-319 (2003).

In Vivo IFN-α Production, Pharmacokinetics and Efficacy

Upon in vitro confirmation of INF-α expression and activity, cultured HUCPVCs are administered to mice intravenously or intraperitoneally. For the study of prophylactic efficacy, mice are challenged one week following HUCPVC administration with a virus (e.g., LCMV). Additionally, some mice are infected with a virus (e.g., LCMV) one week prior to administration of the genetically modified HUCPVCs to assess the therapeutic potential of these cells. Viral titers, derived from blood serum samples, are calculated during the course of the experiment and plotted relative to mice that did not receive HUCPVC/IFN-α treatment to determine in vivo efficacy.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

The invention claimed is:

1. A method for treating or protecting a human subject exposed to a chemical agent comprising administering to the subject a composition comprising an isolated cell population comprising human umbilical cord perivascular cells (HUCPVCs) having a 3G5+, CD45−, CD44+ phenotype,
    wherein the cell population is characterized by rapid proliferation and the presence of human progenitor cells, and the HUCPVCs in said cell population are genetically modified to express a butyrylcholinesterase (BChE) polypeptide or to increase the expression of an endogenous butyrylcholinesterase (BChE) polypeptide, and
    wherein said composition treats or protects said subject exposed to said chemical agent.

2. The method of claim 1, wherein said HUCPVCs are allogeneic or xenogeneic to said subject.

3. The method of claim 1, wherein said chemical agent is selected from a nerve agent, a vesicant, a blood agent, and a respiratory agent.

4. The method of claim 1, wherein said chemical agent is selected from nitrogen mustards, sulfur mustards, acetylcholinesterase inhibitors, Lewisites, saxitoxin, bis(2-chloroethyl)ethylamine, 2-chlorovinyldichloroarsine, 2-chloroethylchloromethylsulfide, bis(2-chloroethyl)sulfide, sarin (GB), cyclosarin (GF), soman (GD), tabun (GA), VX, amiton, PFIB, 3-quinuclidinyl benzilate, phosgene, diphosgene, cyanogens chloride, hydrogen cyanide, and chloropicrin.

5. The method of claim 1, wherein said subject has been exposed to said chemical agent prior to said administering.

6. The method of claim 1, wherein said HUCPVCs are genetically modified to express two or more oligonucleotides or polypeptides.

7. The method of claim 1 further comprising administering one or more therapeutic agents to said subject, wherein said therapeutic agent enhances or prolongs a prophylactic or therapeutic benefit provided upon administration of said isolated cell population comprising HUCPVCs to said subject.

8. The method of claim 7, wherein said therapeutic agent is a cytokine, antiviral agent, immunostimulant, or immunosuppressant.

9. The method of claim 1, wherein said composition comprises a pharmaceutically acceptable carrier or excipient.

10. The method of claim 1, wherein said HUCPVCs are genetically modified to express an RNA interference (RNAi) oligonucleotide capable of inhibiting viral replication or infection.

11. The method of claim 10, wherein said RNAi oligonucleotide is a small inhibitory RNA (siRNA) or short hairpin RNA (shRNA) molecule.

12. The method of claim 1, wherein said HUCPVCs are genetically modified to express a polypeptide selected from an antibody, an antibody fragment, a microbial antigen, a cytokine or growth factor, a hormone, a clotting factor, a drug resistance or anti-viral resistance polypeptide, an anti-venom agent, an antioxidant, a receptor or ligand, an immunomodulatory factor, a detectable label, and a cellular factor.

13. The method of claim 12, wherein said antibody or antibody fragment is a single chain antibody (scFv), Fab, Fab'2, scFv, SMTP, diabody, nanobody, aptamer, or domain antibody;

said cytokine or growth factor is selected from tumor necrosis factor alpha (TNF-α), TNF-β, interferon-alpha (IFN-α), IFN-β, IFN-γ, interleukin 1 (IL-1), IL-1β, interleukin 2-14, granulocyte macrophage colony-stimulating factor (GM-CSF), granulocyte colony-stimulating factor (G-CSF), RANTES, MIP-1α, transforming growth factor-beta (TGF-β), platelet derived growth factor (PGDF), insulin-like growth factor (IGF), epidermal growth factor (EGF), vascular endothelial growth factor (VEGF), keratinocyte growth factor (KGF), erythropoietin (EPO), and thrombopoietin (TPO);

said hormone is selected from angiotensinogen, angiotensin, parathyroid hormone (PTH), basic fibroblast growth factor-2, luteinizing hormone, follicle-stimulating hormone, adrenocorticotrophic hormone (ACTH), vasopressin, oxytocin, somatostatin, gastrin, cholecystokinin, leptin, atrial-natriuretic peptide, epinephrine, norephinephrine, dopamine, calcitonin, and insulin;

said clotting factor is selected from factor VII, factor VIII, factor IX, and fibrinogen;

said enzyme is selected from adenosine deaminase, glucocerebrosidase, alpha-1 antitrypsin, a viral thymidine kinase, hypoxanthine phosphoribosyl transferase, manganese superoxide dismutase (Mn-SOD), catalase, copper-zinc-superoxide dismutase (CuZn-SOD), extracellular superoxide dismutase (EC-SOD), glutathione reductase, phenylalanine hydroxylase, nitric oxide synthetase, and paraoxinase;

said receptor or ligand is selected from a T-cell receptor (TCR), a LDL receptor, surface-bound immunoglobulin, soluble CD4, cystic fibrosis transmembrane conductance receptor (CFTR), and a $F_C$ receptor;

said immunomodulatory factor is selected from CTLA-4, VCP, PLIF, LSF-1, Nip, CD200, uromodulin, CD40L (CD154), FasL, CD27L, CD30L, 4-1BBL, CD28, CD25, B7.1, B7.2, and OX40L;

said detectable label is green fluorescent protein (GFP); or said cellular factor is selected from cytochrome b, ApoE, ApoC, ApoAI, MDR, tissue plasminogen activator (tPA), urokinase, hirudin, β-globin, α-globin, HbA, ras, src, and bd.

14. The method of claim 1, wherein said subject is administered said composition prior to exposure to said chemical agent.

15. The method of claim 3, wherein said chemical agent is a nerve agent.

16. The method of claim 15, wherein said nerve agent is sarin (GB), cyclosarin (GF), soman (GD), tabun (GA), VX, or amiton.

* * * * *